Figure 1:
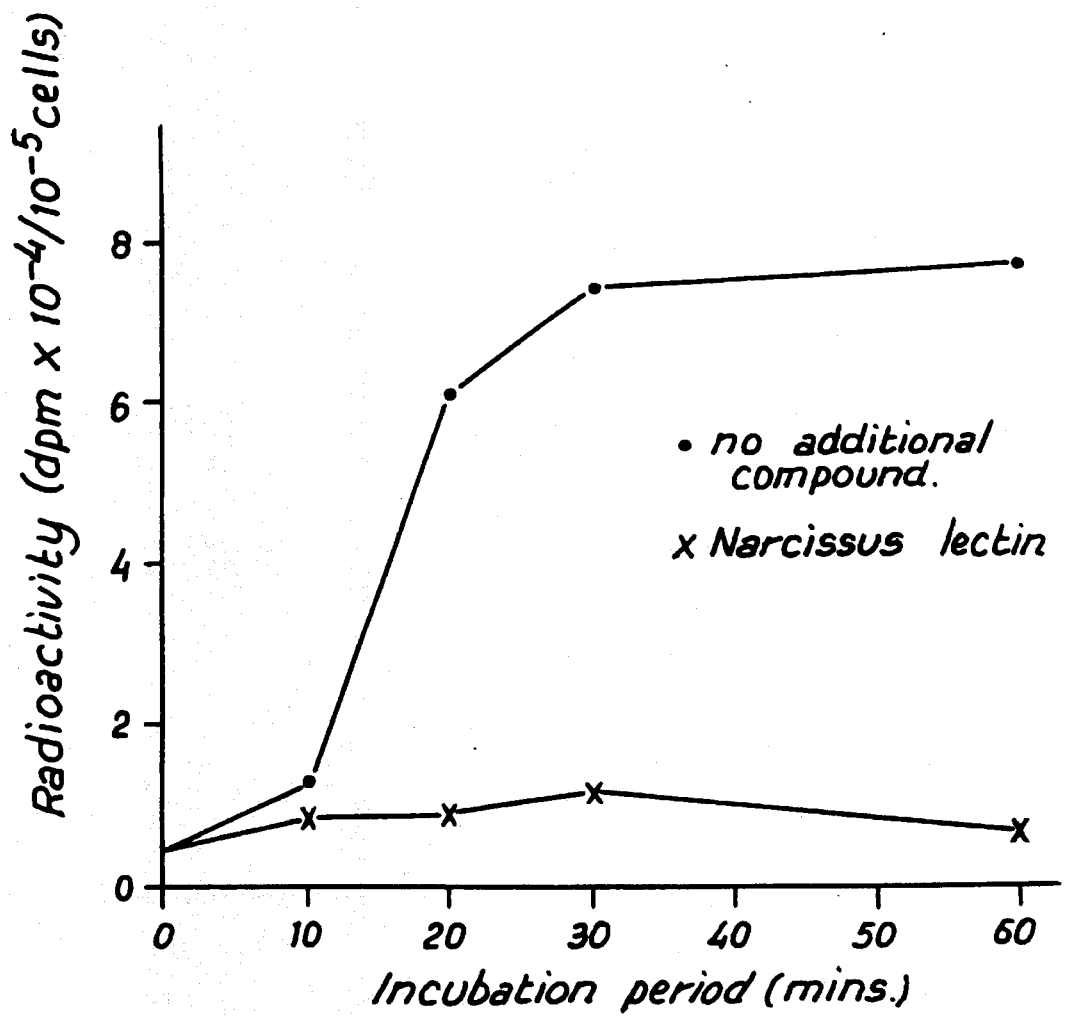

United States Patent [19]

Stewart et al.

[11] Patent Number: 5,462,853
[45] Date of Patent: Oct. 31, 1995

[54] DETECTION OF COMPONENTS OF RNA VIRAL GLYCOPROTEINS USING A MANNOSE-SPECIFIC LECTIN BINDING ASSAY

[75] Inventors: Derek Stewart, Dundee; John M. S. Forrest, Gorsefield, both of Great Britain; Werner Muller, Wiesbaden, Germany

[73] Assignee: Scottish Crop Research Institute, Scotland

[21] Appl. No.: 143,500

[22] Filed: Oct. 22, 1993

Related U.S. Application Data

[63] Continuation of Ser. No. 849,017, filed as PCT/GB90/01638, Oct. 25, 1990, abandoned.

[30] Foreign Application Priority Data

| Oct. 25, 1989 | [GB] | United Kingdom | 8924006 |
| Dec. 2, 1989 | [DE] | Germany | 39 40 009.3 |
| Mar. 28, 1990 | [GB] | United Kingdom | 9006965 |
| May 9, 1990 | [GB] | United Kingdom | 9011263 |

[51] Int. Cl.$^6$ .................................................. C12Q 1/700
[52] U.S. Cl. .......................... 435/5; 435/7.1; 435/7.92; 435/7.93; 435/7.94; 435/7.95; 435/974; 436/501; 436/515; 436/827; 436/518
[58] Field of Search .................... 436/501, 514, 436/515, 827, 518; 435/5, 7.1, 7.92, 7.93, 7.94, 7.95, 974; 530/370

[56] References Cited

FOREIGN PATENT DOCUMENTS

| 173092 | 7/1985 | European Pat. Off. . |
| 295955 | 6/1988 | European Pat. Off. . |

OTHER PUBLICATIONS

Balzarini et al., "Marked Inhibition of Human Immunodeficiencey Virus Type 1 and Type 2 by α–(1–3)–and α–(1–6)–D–Mannose –Specific Plant Lectins", Abstract 65 in Antiviral Research Suppl. 1 Apr. 1990 p. 73.

Moore et al "Sensitive Elisa for the gp/20 and gp/60 Surface Glycoproteins of HIV–1" in AIDS Res. Human Retro. vol. 4 No. 5 (1988) pp. 369–379.

Van Damme et al. "Reltaed Mannose–Specific Lectins from Different Species of the Family Amaryllidacaea" in Physiol. Plant. vol. 73 (1988) pp. 52–57.

Weiler et al, "Human Immunodeficiency Virus: Novel Enzyme–Linked Immunoassays for Quantitation of Envelop Glycoprotein 120" in J. Virol. Methods, vol. 32 (1991) pp. 287–301.

Upjohn, (1983) Virology, Upjohn Co. Kalamazoo, Mich. pp. 40–43.

Robinson et al; AIDS Res & HV Retroviruses 3 (3), 1987.

W. Müller et al, "Narcissus and Gerardis Lectins: Tools for the Development of a Vaccine Against AIDS and a New ELISA to Quantify HIV–gp 120" in *Lectins Cancer,* pp. 27–40, 1991.

Van Damme et al., Chemical Abstracts vol. 109(7), 17 Aug. 1988 p. 275, Abstract No. 5431F.

Muller et al., Journal of Acquired Human Deficiency Syndrome vol. 1(5) pp. 453–458.

Robinson et al., Chemical Abstracts vol. 108(13), 2 Mar. 1988 p. 474 Abstract No. 110641r–and–Aids Research and Human Retroviruses vol. 3(3) 265–82.

Weiler et al. Journal of General Virology vol. 71(9) pp. 1957–1963.

Meruelo et al. Proc. Natl. Acad. Sci USA vol. 85 pp. 5230–5234.

*Primary Examiner*—Carol A. Spiegel
*Attorney, Agent, or Firm*—Ratner & Prestia

[57] ABSTRACT

Anti-viral material comprising a mannose-specific lectin obtained from a bulb of the plant family Amaryllidaceae, for example Narcissus pseudonarcissus, and the use of this material to produce a medicament and a vaccine. The material is effective against RNA viruses which contain glycoproteins with mannose (alpha-1>3) or (alpha-1>6) mannose linkages, for example HIV or HTLV such a Human Immunodeficiency Virus (HIV) and Human T Lymphotropic Virus (HTLV) and can also be used as a diagnostic.

8 Claims, 3 Drawing Sheets

DETECTION OF COMPONENTS OF RNA VIRAL GLYCOPROTEINS USING A MANNOSE-SPECIFIC LECTIN BINDING ASSAY

This application is a continuation of application Ser. No. 07/849,017 filed as PCT/GB90/01638, Oct. 25, 1990 now abandoned.

This invention relates to an anti-viral material and to methods of its use.

Human immunodeficiency virus (HIV) and human T lymphotropic virus (HTLV) have created serious problems throughout the world and it is very important that an effective means of countering them should be found. A large number of materials have been investigated for anti-HIV activity and some have proved to have positive effect; it is desirable to identify materials having anti-HIV activity so that sufficient quantities can be produced for treatment of patients.

It is known that antiretroviral chemotherapy of patients with acquired immunodeficiency syndrome (AIDS) with dideoxynucleosides, such as azidothymidine (AZT), does help some patients. However, the toxicity of AZT, a compound which presumably inhibits viral DNA polymerase in infected cells, is such that new strategies are needed. One strategy is to develop substances that interfere with viral adsorption and penetration by blocking the CD4 receptor or the viral glycoprotein. It has been shown that dextran sulfate is able to block infection of cells by human immunodeficiency virus type 1 (HIV-1). Subsequently, other sulfated polysaccharides, eg heparin sulfate, chondroitin sulfate and polysulfated polyxylan were found to have anti-HIV activity in vitro. These compounds inhibit virus adsorption and syncytium formation though a direct influence of these drugs on the infectivity of virus could not be demonstrated.

Since the pandemic occurrence of AIDS and ATL (adult T-cell leukaemia) there is an urgent need for the development of a diagnostic that will recognise directly HIV and similar viruses, either intact, or as components, especially in body fluids. These viruses are the probable causes of the above diseases.

It has previously been proposed in Journal of Acquired Immune Deficiency Syndromes 1:453–458 by Muller et al to use D-mannose-specific lectin from *Gerardia savaglia* in the prevention of infection of H9 cells within HIV-1. This lectin is obtained by extraction from coral. However, it agglutinates human blood cells and is therefore unsuitable as a therapeutic agent.

The following procedures are basically applicable for the detection of HIV-1 and HTLV:

1. Direct detection on electron microscopical preparations;
2. Visualisation by immunofluorescence using specific antibodies;
3. Detection of viral components by means of genetic probes and hybridisation;
4. Multiplication of virus in cell culture; and
5. Antigen-capture assay (ACA) or competitive capture, for example ELISA.

Until now ACA has only been described in principle: an antibody which recognises the virus or a component of the virus is fixed to a solid phase, eg glass or plastic. Subsequently, human material, preferably serum or plasma is brought into contact with the bound antibody. After adequate incubation, the complex of immobilised antibody and virus (or viral components) can be visualised by a labelled virus-specific antibody.

In competitive capture the antibody is pre-incubated with a test solution which may contain virus or viral components, and is then brought into contact with the same virus or its components bound to a solid phase.

We have found that mannose-specific lectin is capable of recognising the virus or its components with precision.

SUMMARY OF THE INVENTION

According to the present invention there is provided an anti-viral material comprising a mannose-specific lectin obtained from a bulb of the plant family Amaryllidaceae in combination with a pharmaceutical carrier.

Further according to the present invention there is provided a mannose-specific lectin obtained from a bulb of the plant family Amaryllidaceae for use as an anti-viral material.

Still further according to the present invention there is provided the use of a mannose-specific lectin obtained from a bulb of the plant family Amaryllidaceae for the the manufacture of a medicament for the treatment of RNA viruses which contain glycoproteins with mannose (alpha-1→3) or (alpha-1→6) mannose linkages, for example HIV or HTLV. These viruses are preferably terminal (alpha-1→3) or internal (alpha-1→6) or terminal (alpha-1→6) linkages.

Still further according to the present invention there is provided a vaccine for protection against a virus, said vaccine being produced by the use of a mannose-specific lectin obtained from a bulb of the plant family Amaryllidaceae.

Preferably the vaccine is produced by raising antibodies against the lectin, either in in vivo or in vitro, and the antibodies are then used for vaccination against the virus.

Preferably the virus is the HIV or HTLV virus.

The lectin is preferably obtained from narcissus bulbs, and may be for example Narcissus pseudonarcissus lectin (NPL). Other examples of particular lectins are those from Leucojum aestivum and Leucojum vernum. Lectin from NPL is specific for Man (alpha-1→3) Man and Man (alpha-1→6) Man residues. Lectins from snowdrop bulbs may also be effective but may suffer due to their tendency to bind to alpha-2→macroglobulin which is present in human serum in large quantities.

Tests with NPL have proved to be 50% effective in inhibiting HIV infection at 3 ug/ml (about 0.3 uM).

The extraction of the lectins can be conducted in the manner described in Physiologia Plantarum 73:52–57 ("Related mannose-specific lectins from different species of the family Amaryllidaceae") Els J M Van Damme, Anthony K Allen and Willy J Peumans, the disclosure of which is included herein by reference.

The test procedures for the lectins are preferably conducted in the manner described in Journal of Acquired Immune Deficiency Syndromes 1: 453–458 ("The D-mannose-specific Lectin from *Gerardia savaglia* blocks binding of Human Immunodeficiency Virus Type 1 to H9 cells and human lymphocytes in vitro") Werner E G Muller, Karin Renneisen, Matthias H Kreuter, Heinz C Schroder and Irfin Winkler, the disclosure of which is included herein by reference.

Still further according to the invention there is provided a diagnostic material for RNA viruses which contain glycoproteins with Man (alpha-1→3) Man or Man (alpha-1→6) Man linkages or their components, containing a mannose-specific lectin.

The invention is also a diagnostic procedure for RNA viruses which contain glycoproteins with Man (alpha-1→3) Man or Man (alpha-1→6) Man linkages, comprising using the aforementioned diagnostic material in an antigen-capture or competitive capture assay.

The invention also provides a test kit for the detection of RNA viruses Man (alpha-1→3) Man or Man (alpha-1→6) Man linkages or their components, containing a mannose-specific lectin.

The lectins are preferably immobilised on strips of artificial material, glass beads or plastics material. Subsequently the immobilised lectin is incubated for an adequate period with a defined volume of human material, serum or medium. After washing with a solution of neutral pH the lectin-virus (or viral components) complex can be quantified by using antibodies specific for the virus (or its components) in the established procedure "sandwich enzyme-linked immunosorbent assay (ELISA)" (Walker, J M: Methods in Molecular Biology; Volume 1, Urbana Press, Clihton; 1984).

Further, the lectin can be labelled directly. The following labelling procedures can for example be used; radio-active iodine 125, fluorescein isothiocyanate, or an enzyme such as peroxidase (Nowotny, A.: Basic Exercises in Immunochemistry, Springer-Verlag, Berlin; 1979). For quantification, procedures that can be used are: estimation of radioactivity (in the case of radio-labelling), fluorimetry (for fluorescein isothiocyanate labelled antibodies) or enzyme activity with specific substrates (in the above case, hydrogen peroxide).

The accuracy obtained with the new diagnostic is high. Furthermore, it is an advantage that the raw material for this class of lectin is inexpensive.

Embodiments of the invention will now be described by way of illustration in the following Examples.

BRIEF DESCRIPTION OF THE DRAWINGS

FIG. 1 shows the extent of HIV virus binding to MT2 cells in the presence (x) and absence (.) of Narcissus lectin.

FIG. 2 and FIG. 3 schematically illustrate the generation of internal image anti-idiotypic antibodies.

FIG. 4 shows the calibration of the HIV-protein capture assay.

EXAMPLE 1

Lectin from Narcissus pseudonarcissus (NPL) was purified as described by Van Damme et al 1988.

Virus strains

The HTLV-IIIB (Popovic et al, 1984) strain of HIV-1 and two HIV-2 strains, HIV-2ST (Kong et al, 1988) and HIV-$2_{MS}$ (Kanki et al, 1988) were tested.

HIV-1 particles were prepared from the medium of HTLV-IIIB infected H9 cells as described by Popovic et al (1984).

Radiolabelled virus was prepared as follows. Two-week-old HTLV-IIIB infected H9 cells (Popovic et al, 1984) were incubated in medium containing 50 nCi/ml [$^{35}$S]methionine for 2 days. A cell-free supernatant was obtained by low speed centrifugation (4,000 ×g; 10 m min; 4° C.). This was then dialyzed against a 0.1 M Tris-HC1 buffer (pH 7.4; 0.1N NaCl, 0,001M EDTA) for 5 h at 4° C. and virus particles were collected by centrifugation at 30,000 rpm in a Beckman Ti-45 rotor for 2 h (4° C.). The resulting pellet was centrifuged over a 3 ml linear sucrose gradient for 24 h as described (Popovic et al, 1984); the fractions within the density range 1.18 to 1.15 g/ml were collected. The specific radioactivity varied between 1.3 and 2.9× $10^{-16}$ Ci-virion. The particles were counted electron microscopically (Popovic et al, 1984). A second purification procedure, the Nycodenz gradient centrifugation technique, was applied to prepare the virions (Vilmer et al, 1984). After this procedure the specific activity of the virus preparation was found to be identical with the one obtained by sucrose gradient centrifugation. This is one indication that no cellular membranes had cosedimented with the virus particles.

Cells and virus infection

The human T-cell lines MT-2 (Harada et all, 1985), CEM (Nara and Fischinger, 1988), ATH8 (Mitsuya and Broder, 1986) and H9 (Popovic et al, 1984) the human monocyte line U937 (Ezekovitz et al, 1989) and the somatic cell hybrid culture between CEM and the B cell line 174 (Kong et al, 1988) were grown in RPMI 1640 medium supplemented with 15% (v/v) fetal calf serum (Muller et al, 1988). Cultures were maintained at 37° C. in a humidified atmosphere at 5% $CO_2$ in air.

HIV-1 infection: The cells were routinely seeded at a concentration of $1\times10^5$ cells/ml and HIV-1 virus was added to give a multiplicity of infection (MOI) of 0.03 medium tissue culture infectious dose ($TCID_{50}$) per MT-2 cell and 0.12 $TCID_{50}$ per CEM or U937. The cells were incubated in the presence or absence of the test compounds for 7 days. During that time the uninfected MT2 cells performed 2.91 doubling steps, CEM cells 2.14 doublings and U937 cells 1.93 doublings. The infected cells underwent the following doubling steps; MT-2/HTLV-IIIB: 0.09, CEM/HTLV-IIIB: 0.04; and U937/HTLV-IIIB: 0.08.

Unless mentioned otherwise, clarified conditioned HIV-1 culture fluid was pretreated (30 min at 36° C.) with the different compounds and then added to the cells to yield the indicated compound and virus concentrations. The virus preparation was preincubated together with the compound in a volume of 100 ul and hence in a ten-fold higher concentration than the one finally present in the cell culture experiment.

HIV-2 infection: HIV-$2^{ST}$ producing CEMx174 cells and HIV-$2_{MS}$ producing U937 cells were irradiated with 10,000 rad and then cocultivated at a density of $4\times10^4$ cells/ml final assay volume with $2\times10^5$ ATH8 cells. After 7 days incubation only the ATH8 cells were alive and their densities were estimated. The test compounds were added to the irradiated cells 30 mins prior to the addition of the ATH8 cells. In the uninfected controls the ATH8 cells underwent 2.01 doubling steps during the 7-days incubation.

Evaluation: Cell concentrations were routinely evaluated using the XTT colorimetric assay system (Scudiero et al, 1988) followed by evaluation with an ELISA-reader (Bio-RAD, model #3550, equipped with the program NCIMR IIIB). To standardize the growth curves, the cells were counted electronically (Cytocomp Counter; Model Michaelis). The number of doubling steps was determined as described (Muller et al, 1975).

The 50% cytoprotective concentration ($IC_{50}$) represents that concentration at which cell growth of HIV-infected cells reached 50% of the growth rate of the uninfected cells during the incubation period of 7 days. The 50% cytotoxic concentration ($TC_{50}$) represents that concentration at which the growth rate of the infected cells was reduced by 50%; this value is usually similar to the $TC_{50}$ of uninfected cells. The 50% values were estimated by logit regression (Sachs, 1984). The antiviral index (AI) is calculated from the ratio $TC_{50}$:$IC_{50}$.

Syncytium induction assay

This assay was performed as described (Matthews et al 1987). A total of $1\times10^5$ HTLV-IIIB-infected H9 cells were mixed with 1×10⁵ uninfected Jurkat cells in a final volume of 100 ul either in the presence or the absence of the compound. Five and 24 hours later, syncytium formation (defined as >4 nuclei within a common cell membrane) was semiquantitatively scored (Lifson et al, 1986): −, no syncytia; 1+; rare small syncytia; 2+, multiple moderately sized syncytia; 3+, large syncytia in most, but not all microscope fields (magnification 400 ×); and 4+, numerous large syncytia in all fields examined.

Virus-cell binding studies

1×10⁵ MT-2 cells were suspended in 1 ml of binding assay buffer (20 mM Na-phosphate, 1 mM $CaCl_2$, 130 mM NaCl, 2% (w/v) bovine serum albumin [Muller et al]), 1982]). Then 20 ul of labelled virus (approximately 25×10⁴ dpm/assay [final]) were added and incubated for 0 to 60 min at 37° C. in 5% $CO_2$. The cells were subsequently washed by centrifugation (2,000×g; 10 min; 4° C., and radioactivity was counted.

the syncytium-induction assay strongly inhibited syncytium formation (Table 2). At a concentration of 3 ug/ml of the lectin no syncytium formation could be measured.

Inhibition of HIV-1 binding to MT-2 cells by Narcissus lectin

Further, addition of Narcissus lectin (20 ug/ml) almost completely abolished the binding of HIV-1 [HTLV-IIIB] particles to MT-2 cells FIG.1 shows the effect on the binding of HIV-1 to MT-2 cells of Narcissus lectin. [$^{35}$S]methionine-labelled HIV-1 [HTLV-IIIB] was incubated with MT-2 cells either in the absence of any additional compound or in the presence of 20 ug/ml of Narcissus lectin. The samples were taken after 0–60 min and the radioactivity, bound to MT-2 cells, was determined as described.

This Example demonstrates the function of NPL in binding to HIV and in preventing infection of cells by HIV-1 and HIV-2.

TABLE 1

| Compound | $IC_{50}$ ug/ml | $TC_{50}$ ug/ml | AI | $IC_{50}$ ug/ml | $TC_{50}$ ug/ml | AI | $IC_{50}$ ug/ml | $TC_{50}$ ug/ml | AI |
|---|---|---|---|---|---|---|---|---|---|
| | | | | HIV-1 | | | | | |
| | MT-2/HTLV-IIIB | | | CEM/HTLV-IIIB | | | U937/HTLV-IIB | | |
| AZT | 0.008 | 11.7 | 1462 | 0.014 | 12.8 | 914 | 0.078 | 9.5 | 122 |
| NPL | 4.97 | >100 | >20 | 2.18 | >100 | >46 | 7.31 | >100 | >14 |
| | | | | HIV-2 | | | | | |
| | CEMX174/HIV-2$_{ST}$ | | | | | | UP37/HIV-2$_{MS}$ | | |
| AZT | 0.023 | 8.7 | 378 | | | | 0.094 | 9.1 | 97 |
| NPL | 6.58 | >100 | >15 | | | | 8.57 | >100 | >12 |

Where indicated the virus preparation (20 ul) was preincubated for 1 h at 4° C. with a 10 ul solution of Narcissus lectin and then added to the cells.

Binding studies

Binding to uninfected MT-2 cells or HTLV-IIIB-infected MT-2 cells [infection was performed for 3 days as described above] was determined similarly. MT-2 cells (1×10₅), in a final volume of 1 ml binding buffer, were preincubated for 30 min at 4° C. Then the cell suspension was washed twice by centrifugation (2,000× g; 10 min; 4° C.) and the cells were incubated (1 hr at 4° C.) in an 1-ml volume in the presence or absence of 1 mM $Ca^{2+}$ with NPL. Finally the cells were washed twice with binding buffer by centrifugation and the cell-associated radioactivity was determined. The background value (assay without cells but in the presence of $Ca^{2+}$) was, 50 dpm ml.

Anti-HIV activity of Narcissus lectin

The Narcissus lectin was tested for anti-HIV activity firstly by applying the cytoprotection assay; cell density was determined by the XTT tetrazolium/formazan assay. As shown in Table 1 the mannose specific Narcissus lectin displayed a considerable anti-HIV-1 cytoprotective effect with an AI between >14 and >46. In the CEM ×174/HIV-2$_{ST}$ and the U937/HIV-2$_{MS}$ systems the AI was determined to be >15 and >12, respectively. In addition, NPL displayed no cytotoxic effects up to 100 ug/ml, while AZT caused a 50% cytotoxic effect at concentrations around 9 ug/ml (Table 1). For reasons of comparison, inhibitory activity of AZT against HIV-1 and HIV-2 is included in the Table.

Inhibition of syncytium formation by Narcissus lectin

Addition of Narcissus lectin during the coincubation period of Jurkat cells with HTLV-IIIB producing H9 cells to

TABLE 2

| | Concentration | Syncytium formation | |
|---|---|---|---|
| Compound | (ug/ml) | 5 h | 24 h |
| None | — | 4 + | 4 + |
| NPL | 0.3 | 3 + | 3 + |
| | 1.0 | 1 + | 1 + |
| | 3.0 | — | — |

The effect on the binding of HIV-1 to MT-2 cells of Narcissus lectin is illustrated in FIG. 1. [$^{35}$S] methionine-labelled HIV-1 [HTLV-IIIB] was incubated with MT-2 cells either in the absence of any additional compound (line .) or in the presence of 20 ug/ml of Narcissus lectin (line X). The samples were taken after 0–60 min and the radioactivity, bound to MT-2 cells, was determined as described in the Example.

Figure 2:
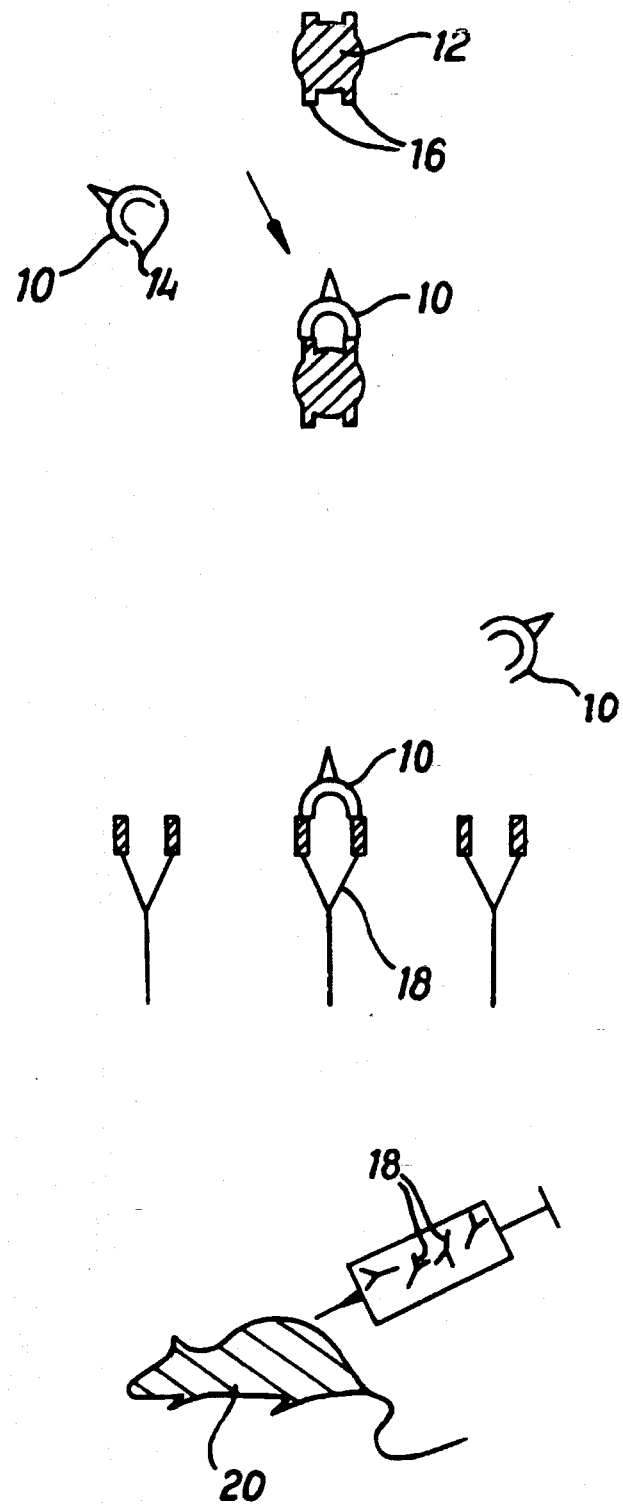

FIG. 2 illustrates graphically the generation of internal image anti-idiotypic antibodies for use in treatment against infection by HIV. The lectin NPL is shown as 10 and is capable of binding with the envelope glycoprotein of the HIV virus 12 through receptor sites 14, 16. The lectin can therefore be introduced into a recipient mouse which creates anti-lectin antibodies 18. Some of these anti-bodies 18 mimic the virus envelope glycoprotein receptor site and are selected by affinity chromatography and their ability to give rise to antiidiotypic antibodies which mimic the lectin, as described in Weiler et al, 1990; Journal of General Virology.

The selected antibodies can then be used as a vaccine or to immunise syngenetic mice 20 to produce anti-antilectin antibodies for the treatment of infected patients. Alternatively the selected antibodies may be used to produce anti-antilectin antibodies by cultivation in vitro with cells from the mouse spleen.

Use of the compound NPL to raise a vaccine against HIV or similar viruses may be achieved by purifying the compounds with high performance liquid chromatography (HPLC) or affinity chromatography and using them to raise murine antibodies by an appropriate route of immunisation.

If the products are of low antigenicity they may also be coupled to carrier proteins prior to immunisation, or failing that, used to immunise murine cell lines in vitro (Vaux et al, 1988; Nature 336, 36–42).

Antibodies which mimic the internal image of the viral receptor site may then be selected by affinity chromatography and/or the ability to produce active anti-idiotypic antibodies (Weiler et al, 1990; Journal of General Virology, in press).

Finally, the vaccine may be administered by a suitable route in conjunction with immunostimulating complexes or other adjuvants (Takahashi et al, 1990; Nature 344, 873–875).

Figure 3:
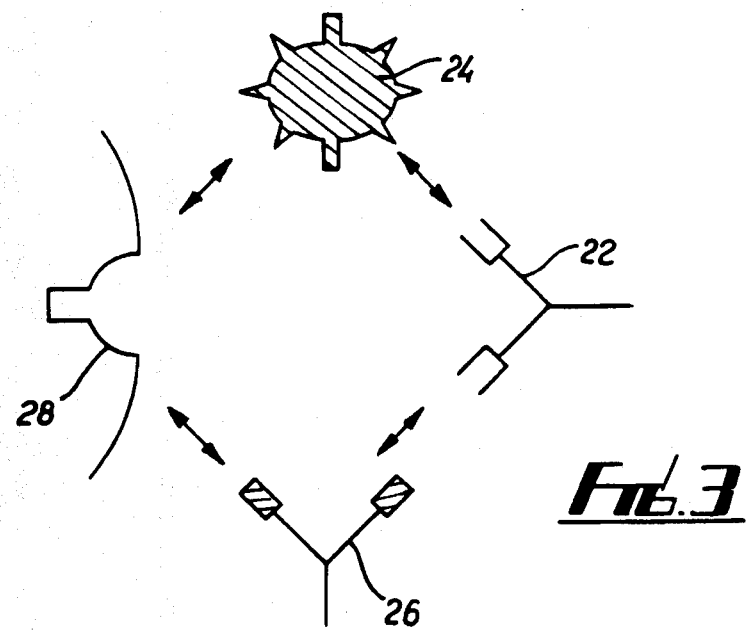

Referring to FIG. 3, virus 24, which binds to a site on the host membrane 28, can be used as immunogen to produce a library of anti-viral monoclonal antibodies 22 in a mouse. The monoclonal antibody 22 against receptor binding site on the virus 24 is selected because of its neutralisation ability. When the anti-viral monoclonal antibody 22 is injected into a syngenetic recipient mouse, anti-antibodies (anti-idiotypic antibodies) 26 are produced with specificity to the antigen binding site 28 of the anti-viral monoclonal antibody 22. A subset of the anti-idiotypic antibodies 26 will possess conformational similarities to the receptor binding site of the primary virus. Such "internal image" anti-idiotypic antibodies 26 therefore react with the cell membrane receptor.

Furthermore, immunisation with such "internal image" anti-idiotypic antibodies 26 will give rise to anti-antiidiotypic antibodies, some of which react specifically with the binding site on the virus 24.

For example, once the lectin has been purified it may be injected into a mouse which produces anti-lectin antibodies. These antibodies may be used in a number of ways eg to immunise a second mouse in vivo, or in vitro by taking cells from the mouse spleen and cultivating in vitro.

Further examples will now be given to illustrate the use of the invention in diagnosis.

EXAMPLE 2

The lectin from the plant *Narcissus pseudonarcissus* can be isolated as described by van Damme et al, 1988. This lectin specifically recognises D-mannose.

Its detection as a diagnostic was achieved by the Ouchterlony/double gel diffusion assay (Ouchterlony, O.; Acta Pathol. Microbiol, Scand, 26: 507, 1949). 1% agar in physiological saline was dispensed into glass dishes and allowed to solidify. Subsequently wells of 3 mm diameter were stamped out at a distance of 7 mm. In one well 20 ul of lectin (2 ug/ml) was placed, and in the neighbouring well 20 ul viral protein (2 ug/ml). The viral protein chosen was gp120 from HIV-1. gp120 was isolated as described by Matthews et al, 1987. The dish was allowed to stand for 2 days at room temperature in a moist chamber, after which a precipitation line was clearly visible. The formation of such a precipitate is the clear indication of a typical specific recognition reaction.

EXAMPLE 3

HIV virus and its components react specifically with lectin in a double gel diffusion test. In this Example, it is demonstrated that the Narcissus lectin can be included in a diagnostic procedure.

The wells of a polystyrene microtitre plate (96 wells with flat bottoms) were loaded with 100 ul of a Narcissus lectin solution (20 ug/ml in physiological saline). The plates were incubated for 16 hours at room temperature. The wells were then washed with a 0.5% aqueous solution of Tween 80 (polyoxyethylenesorbitan mono-oleate) containing 0.1M NaCl and 0.02M Tris [hydroxymethyl] aminomethane, pH 7.4. Tween 80 was obtained from Sigma, St Louis, Mo., USA) to remove unbound lectin. The wells were then filled with 100 ul of the test solution (See below; the serum of an AIDS patient or a solution of the HIV-1 protein gp120. After incubation for 8 hours at room temperature, they were washed sufficiently (3×5 mins) with the above Tween 80 to remove unbound material. Subsequently, 100 ul of polyclonal antibody against HIV-1 specific gp120 was added to the wells (the polyclonal antibody which was raised in rabbits, was obtained from Fa Biochrome, Berlin). The antibody used in this procedure was biotinylated; it was used at a concentration of 10 ng/ml. After incubation at room temperature for 60 min the wells were again washed with Tween solution (3×5 mins) and incubated with 100 ul of 1:500 avidin-peroxidase solution (Sigma Ltd) for a further 60 min. The wells were then washed with Tween solution (3×5 mins) and loaded with 100 ul of the peroxidase substrate. This consisted of 0.03% aqueous hydrogen peroxidase solution and ethanolic 8 mM 4-chloro-1-naphthol solution (mixed 1:1). After incubating for one hour at room temperature, the absorbance at wavelength 414 nm was measured by photometer. In the following table the results of a typical experiment are shown.

TABLE 3

| Test solution | Dilution | Concentration (ng/ml) | Extinction at 414 nm |
| --- | --- | --- | --- |
| Serum of an | 1:1 | | 3.68 |
| AIDS patient | 1:2 | | 1.82 |
| | 1:4 | | 0.85 |
| | 1:8 | | 0.43 |
| | 1:16 | | 0.18 |
| | 1:32 | | 0.09 |
| gp120 | | 0.05 | 1.39 |
| | | 0.025 | 0.64 |
| | | 0.0125 | 0.32 |
| | | 0.005 | 0.12 |
| | | 0.0025 | 0.06 |

The absorbance was measured against a blank (control serum from a healthy person or human serum albumin) or the same concentration.

From the table it is evident that the antigen-capture assay described was able to detect the presence of HIV-1 virus or one of its antigens, gp120, with precision.

EXAMPLE 4

The inclusion of the lectin from Narcissus pseudonarcissus in a HIV-protein based capture assay.

Polyvinylchloride 96-well microtiter plates (Costar) were coated with 0.1 ml of HIV-protein [10 ug/ml in 0.1M Na-carbonate buffer (pH 9.6)]. After incubation for 12 hr at 4° C. in a humid atmosphere the protein solution was removed and the wells were filled with dilution buffer (3% bovine serum albumin in phosphate buffered saline [PBS] supplemented with 1 mM $CaCl_2$ and 0.02% Na-azide). After further incubation for 2 hr at 20° C. the plates were washed twice with PBS.

Subsequently the plates were incubated with 100 ul of antigen test solution for 2 hr at 37° C. The antigen test solution was composed of 50 ul of a constant amount of alkaline phosphatase coupled Narcissus pseudonarcissus lectin NPL (5 ng) and 50 ul of increasing concentrations of free gp120 (0 to 10 ng) in dilution buffer (see above). Prior to the addition to the HIV-protein coated wells the test solution, composed of NPL and free gp120 was preincubated (2 hr; 20° C.) in a humid atmosphere.

In one series of experiments the 50 ul of enzyme coupled NPL was added first to the coated well. After a washing step with PBS 50 ul free gp120 was added 10 min later in this sequential manner.

After incubation of the HIV-protein-coated plates (i) with a sample of the preincubated material [NPL and free gp120] or (ii) after a sequential addition of the components (first incubation of the plates with NPL and after a washing step with gp120) for 60 min at 37° C., the wells were washed twice with 0,05% Tween 20 in PBS and then twice with 10 mM diethanolamine (pH 9.5, containing 0.5 mM $MgCl_2$). After drying the plates 50 ul of alkaline substrate solution (p-nitrophenyl phosphate) was added. The reaction was stopped by addition of 50 ul 0.1M EDTA and the absorbance was read at 405 nm in an ELISA reader.

Figure 4:
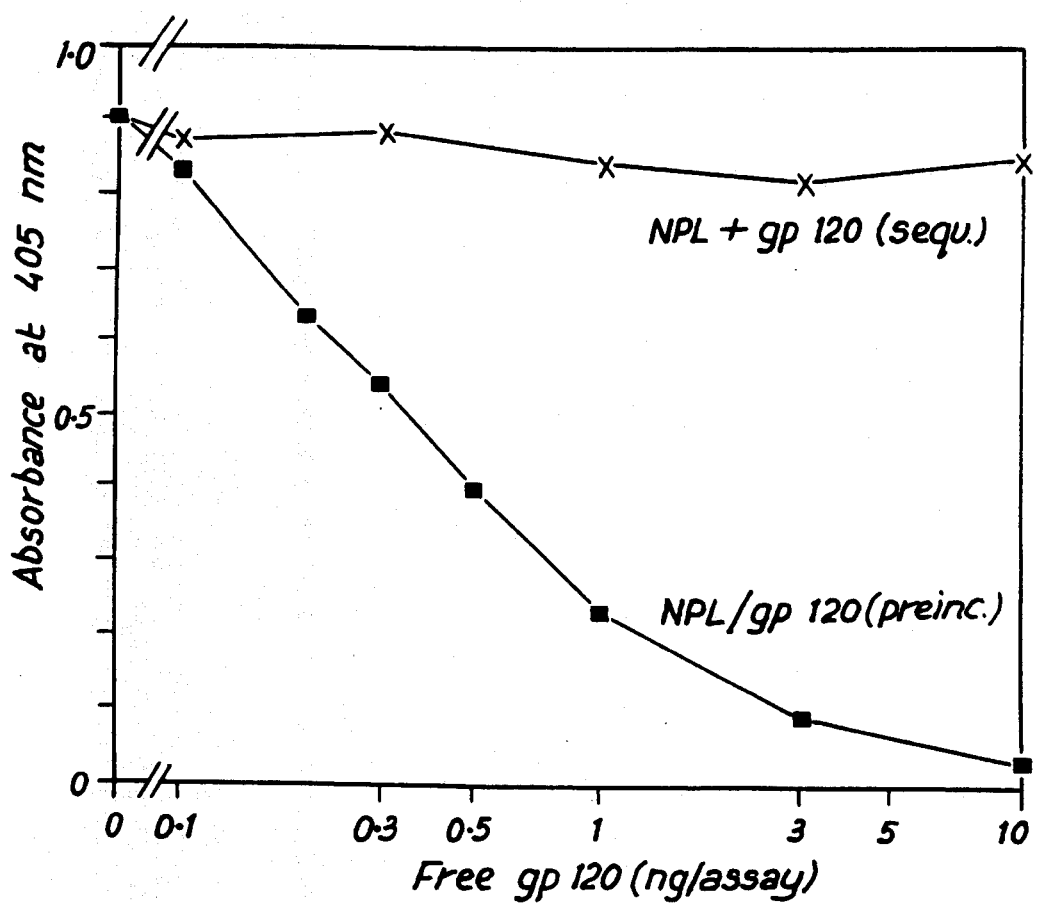

FIG. 4 Calibration of the HIV-protein based capture assay. HIV-protein coated wells of microtiter plates were incubated with a constant amount of alkaline phosphatase coupled NPL (Narcissus pseudonarcissus lectin) (5 ng) and increasing amounts of free gp120 (0–10 ng). The components were added in two different ways, (i) NPL and gp120 were first preincubated and then added to the coated wells [NPL/gp120 (preinc)] or (ii) the components were added sequentially, first NPL was added to the coated wells and subsequently gp120 was added [NPL+gp120 (sequ)]. After incubation and the subsequent addition of the alkaline phosphatase substrate solution the immunocomplexes bound to the solid support were quantified by reading the absorbance in an ELISA reader. The means of five parallel experiments are given; the SD was less than 12%.

BIBLIOGRAPHY

Ezekovitz R A, Kuhlman M, Groopman J E and Byrn R A (1989) A human serum mannose-binding protein inhibits in vitro infection by the human immunodeficiency virus. Journal of Experimental Medicine 169, 185–196.

Harada S, Koyanagi Y and Yamamoto N (1985) Infection of HTLV-III/LAV in HTLV-I-carrying MT-2 and MT-4 and application in a plaque assay. Science 229, 563–566.

Kanki P, Barin F and Essex M (1988) Antibody reactivity to multiple HIV-2 isolates. Fourth International Conference on AIDS; Stockholm; Abstract #1659.

Kong L I, Lee S W, Kappes J C, Parkin J S, Decker D, Hoxie J A, Hahn B H and Shaw G M (1988) West african HIV-2-related human retrovirus with attenuated cytopathicity. Science 240, 1525–1529.

Lifson J, Contre S, Huang E and Engleman E (1986) Role of envelope glycoprotein carbohydrate in human immunodeficiency virus (HIV) infectivity and virus-induced cell fusion. Journal of Experimental Medicine 164, 2101–2106.

Matthews T J, Weinhold K J, Lyerly H K, Langlois A J, Wigzell H and Bolognesi D P (1987) Interaction between the human T-cell lymphotropic virus type IIIB envelope glycoprotein gp120 and the surface antigen CD4; role of carbohydrates in binding and cell fusion. Proceedings of the National Academy of Sciences, USA 84, 5424–5428.

Mitsuya H and Broder S (1986) Inhibition of the in vitro infectivity and cytopathic effect of human T-lymphotropic virus type III/lymphadenopathy-associated virus (HTLV-III/LAV) by 2', 3'-dideoxynucleosides. Proceedings of the National Academy of Sciences 83, 1911–1915.

Muller W E G, Rohde H J, Steffen R, Maidhof A, Bachmann M, Zahn R K and Umezawa H (1975) Influence of formycin-B on polyadenosine diphosphoribose synthesis in vitro and in vivo. cancer Research 35, 3673–3681.

Muller W E G, Schuster D K, Zahn R K, Maidhof A, Leyhausen G, Falke D, Koren R, and Umezawa, H (1982) Properties and specificity of binding sites for the immunomodulator bestatin on the surface of mammalian cells. International Journal of Immunopharmacology 4, 393–400.

Muller W E G, Renneisen K, Kreuter M H, Schoder H C and Winkler I (1988) The D-mannose-specific lectin from *Gerardia savaglia* blocks binding of human immunodeficiency virus type I to H9 cells and human lymphocytes in vitro. Journal of Acquired Immune Deficiency Syndromes 1, 453–458.

Nara P L, and Fischinger P J (1988) Quantitative infectivity assay for HIV-1 and -2. Nature 332, 469–470.

Poiesz B J, Ruscetti F W, Gazdar A F, Bunn P A, Minna J D and Gallo R C (1980) Detection and isolation of type C retrovirus particles from fresh and cultured lymphocytes of a patient with cutaneous T-cell lymphoma. Proceedings of the National Academy of Sciences, USA 77, 7415–7419.

Popovic M, Sarngadharan M G, Read E and Gallo R C (1984) Detection, isolation and continuous production of cytopathic retroviruses (HTLV-III) from patients with AIDS and pre-AIDS. Science 224, 497–500.

Sachs L (1984) Angewandte Statistik. Berlin: Springer Verlag; pp 209–216.

Schroder H C, Wenger R, Kuchino Y and Muller W E G (1989) Modulation of nuclear matrix-associated (2'-5')oligoadenylate metabolism and ribonuclease L activity in H9 cells by human immunodeficiency virus. Journal of Biological Chemistry 264, 5669–5673.

Scudiero D A, Shoemaker R H, Paull K D, Monks A, Tierney S, Nofziger T H, Currens M J, Seniff D and Boyd M R (1988) Evaluation of a soluble tetrazolium/formazan assay for cell growth and drug sensitivity in culture using human and other tumor cell lines. Cancer Research 48, 4827–4823.

Van Damme E J M, Allen A K and Peumans W J (1988) Related mannose-specific lectins from different species of the family Amaryllidaceae. Physiologia Plantarum 73, 52–57.

Vilmer E, Barre-Sinoussi F, Rouzioux C, Gazengel C, Brun F V, Dauguet C, Fischer A, Manigne P, Chermann J C, Griscelli C and Montagnier L (1984) Isolation of new lymphotropic retrovirus from two siblings with haemophilia B, one with AIDS. Lancet I, 753–757.

We claim:

1. An in vitro assay for determining the presence or amount of components of RNA vital glycoproteins with mannose-mannose linkages selected from the group consisting of α-1→3 and α-1→6 mannose-mannose linkages in a sample suspected of containing said components, the assay comprising:

providing an Amaryllidaceae-derived lectin which specifically binds to mannose-mannose linkages selected from the group consisting of $\alpha$-1→3 and $\alpha$-1→6 mannose-mannose linkages;

contacting said samples with said lectin to form specific binding complexes between said lectin and any of said components in said sample;

determining the presence or amount of said specific binding complexes; and, correlating the presence or amount of said specific binding complexes to the presence or amount of said components in said sample.

2. The assay as claimed in claim 1, wherein said specific binding complexes are immobilised on a surface, and said assay further includes the steps of:

contacting said immobilised specific binding complexes with an enzyme-linked binding protein to form a further complex between said enzyme-linked binding protein and said specific binding complex;

washing said surface to remove unbound binding protein;

contacting said further complex with a substrate for the enzyme moiety of said enzyme-linked binding protein; and measuring the effect of said enzyme moiety on said substrate and correlating said effect to the presence or amount of said components in said specific binding complexes.

3. The assay as claimed in claim 1, wherein at least one of the reactants selected from the group consisting of said components and said lectin diffuses through a gel to contact the other of said reactants, thereby to form said specific binding complexes.

4. The assay as claimed in claim 1, wherein the amount of said specific binding complexes is correlated to the amount of said components by comparison of said amount of said specific binding complexes to a known amount of said components.

5. The assay as claimed in claim 1, wherein said components are immobilised on a surface and said specific binding complexes are formed by said immobilised components and said lectin, said lectin having an enzyme linked thereto, and wherein said assay includes the steps of:

washing said surface to remove any enzyme-linked lectin not comprised in said specific binding complexes;

contacting said specific binding complexes with a substrate for said enzyme; and, measuring the effect of said enzyme on said substrate and correlating said effect to the presence or amount of said components in said specific binding complexes.

6. The assay as claimed in claim 1, further including the steps of contacting said specific binding complexes with an enzyme-conjugated antibody which binds specifically to said specific binding complexes to form a further complex of said antibody and said specific binding complex, washing said further complexes to remove unbound antibody, and subsequently exposing to said further complex of said antibody and said specific binding complexes a substrate for said enzyme, whereby the relative amount of components in said specific binding complexes is determined by measuring the effect of said enzyme on said substrate and comparing said effect to a known standard.

7. The assay as claimed in claim 1, wherein said lectin is derived from *Narcissus pseudonarcissus*.

8. The assay as claimed in claim 1, wherein said lectin is derived from a bulb.

* * * * *